(12) United States Patent
Ravin et al.

(10) Patent No.: US 7,276,367 B2
(45) Date of Patent: Oct. 2, 2007

(54) METHOD OF ETCHING ISLANDS OF CELLS IN A GRID PATTERN

(75) Inventors: Rea Ravin, Rockville, MD (US);
James V. Sullivan, Bowie, MD (US);
Daniel Hoeppner, Bethesda, MD (US);
David W. Munno, Stamford, CT (US);
Ron McKay, Bethesda, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 35 days.

(21) Appl. No.: 10/967,703

(22) Filed: Oct. 14, 2004

(65) Prior Publication Data

US 2006/0084051 A1 Apr. 20, 2006

(51) Int. Cl.
*C12M 1/00* (2006.01)
(52) U.S. Cl. ............... 435/284.1; 435/4; 436/807; 216/96; 216/97
(58) Field of Classification Search ............ None
See application file for complete search history.

(56) References Cited

U.S. PATENT DOCUMENTS 5,976,826 A * 11/1999 Singhvi et al. ............ 435/29
6,133,030 A 10/2000 Bhatia et al.
6,368,838 B1 4/2002 Singhvi et al.
7,033,821 B2 * 4/2006 Kim et al. ............... 435/288.4
2003/0003571 A1 * 1/2003 Kanegasaki et al. ..... 435/288.5

FOREIGN PATENT DOCUMENTS

WO WO 01/70389 A1 9/2001

OTHER PUBLICATIONS

Xia, Younan et al.; "Unconventional Methods for Fabricating and Patterning Nanostructures"; 1999, *Chem. Rev.*, vol. 99, 1823-1848.

* cited by examiner

*Primary Examiner*—Anish Gupta
*Assistant Examiner*—Julie Ha
(74) *Attorney, Agent, or Firm*—Townsend and Townsend and Crew, LLP; Guy W. Chambers (57) ABSTRACT

An apparatus and process for monitoring migratory cell proliferation with restricted migration on a substrate includes providing a substrate, coating the substrate with extracellular matrix, plating cells suspended in cell culture media on extracellular matrix, and placing intersecting channels across the extracellular matrix components by removing the extracellular matrix components from the channels to isolate islands of the extracellular matrix components on the substrate. When the cells are immersed with a fluid, migration of the cells is confined to the isolated islands of the extracellular matrix components, permitting long-term observation of a migratory population.

5 Claims, 9 Drawing Sheets

METHOD OF ETCHING ISLANDS OF CELLS IN A GRID PATTERN

STATEMENT AS TO RIGHTS TO INVENTIONS MADE UNDER FEDERALLY SPONSORED RESEARCH OR DEVELOPMENT

The technology set forth herein is federally sponsored and funded by the United States Department of Health and Human Services. The United States government has certain rights in this invention.

CROSS-REFERENCES TO RELATED APPLICATIONS

REFERENCE TO A "SEQUENCE LISTING," A TABLE, OR A COMPUTER PROGRAM LISTING APPENDIX SUBMITTED ON A COMPACT DISK

BACKGROUND OF THE INVENTION

This invention relates to monitoring the proliferation of migratory cells such as CNS stem cells/embryonic stem cells or any other migratory cells. More specifically, an apparatus and process is disclosed for placing isolated islands of an extracellular matrix on a glass cover slip, and, plating, growing, and monitoring the proliferation of migratory cells on the isolated islands of the extracellular matrix.

Migratory cells, such as CNS stem cells/embryonic stem cells or any other migratory cells are grown and simultaneously monitored during proliferation for research purposes. Typically, an extracellular matrix is placed upon a substrate, usually a coverslip. Thereafter, cells are plated to (placed on) the extracellular matrix for observation during proliferation. During this observed proliferation, the cells unfortunately also migrate.

Migration causes problems. Typically, only a discrete area on a substrate, such as a portion of a substrate having the extracellular matrix, can be observed. During migration, cells within the observed discrete area move out of the observed discrete area; what becomes of such cells is never known to the observer. Other foreign cells, initially outside of the observed discrete area, move into the observed area; as a consequence, the beginning history of such cells can never be known to the observer. In either case, the integrity of the monitoring processes is degraded. Where one wishes to have an observed history of the proliferation of a group of monitored cells, migration of the cells into or out of the observed area must be inhibited.

For this reason, where cell populations are grown on substrates, such as glass cover slips, attempts have been made to provide isolated islands of substrate. These isolated islands of substrate have the effect of allowing cell migration within their boundaries while maintaining a discrete cell population within an observable area.

Attempts to create isolated islands has included printing glass cover slips with the desired isolated islands. In this technique, the material from which the extracellular matrix is ultimately formulated is placed upon a printing block having printing areas shaped with the desired profile of isolated islands of extracellular matrix. Thereafter, the printing block is impressed upon a substrate, such as a glass cover slip, to transfer the extracellular matrix material from the print block to the glass cover slip. Substrate material is transferred from the printing block onto the glass cover slip much as printer's ink is transferred from a printing block onto paper which is to be printed. The extracellular matrix transferred to the substrate has the profile of the printing areas on the printing block.

Other techniques have included photo lithographic masks utilizing photo resist, contact masks, micro stamping, and ink jet printing.

For many of these techniques to work, drying of the substrate transferred on the glass cover slip from the printing block is required. Unfortunately, drying substantially degrades or destroys the extracellular matrix. The growth of cells for subsequent observation is difficult. Further, many of these techniques leave residual chemicals (such as photo resist) with the deposited substrate. These residual chemicals degrade the subsequent growth on the substrate. Most importantly, these techniques do not permit plating of the migratory cells before formation of the islands of substrate.

It has also been contemplated to utilize lasers to form continuous channels upon a continuous layer of extracellular matrix on a glass cover slip. In this technique, the extracellular matrix is placed upon a substrate, typically a glass cover slip. Once the extracellular material is placed, at least one laser is utilized to etch channels in the extracellular matrix. Typically, the extracellular matrix is submerged during laser etching of channels. This provides isolated islands of extracellular matrix having separation between isolated islands complimentary to the channel width and placement on the substrate.

The technique suffers from several disadvantages.

Utilizing lasers to make such channels is expensive. Further, the ablation of the extracellular matrix generates debris and produces localized heating at the channel boundaries which can damage the extracellular matrix adjacent the channel boundaries. Further, if cutting of the channels occurs while the matrix is submerged in a liquid, localized heating of the substrate will occur.

BRIEF SUMMARY OF THE INVENTION

An apparatus and process for monitoring migratory cell proliferation with reduced migration on a substrate includes providing a substrate, such as a glass coverslip. The substrate is coated with extracellular matrix. Plating the extracellular matrix with migratory cells then occurs. Finally, intersecting channels are placed across the plated extracellular matrix by mechanical etching to form desired isolated islands for the observation of migratory cell growth. When the plated cells within the isolated islands are immersed with a growth media, migration of the cells is confined to the isolated islands of the substrate. By observing the isolated islands during cell growth, cell characteristics of migratory cells can be observed.

In the following specification, we use the word "substrate" to describe the surface on which the extracellular matrix is placed. The reader will understand that this is almost always a coverslip used for magnified observation of the migratory cell proliferation.

Further, we do not emphasize the normal step of conjugating a fluorescent dye to the extracellular matrix in order to render the extracellular matrix visible and provide the necessary light for observing cell proliferation. As this step is conventional in observations of cellular proliferation, it will not be further discussed herein.

An advantage of this invention is that the formation of the isolated islands of extracellular matrix upon a glass cover slip is carried out in a continually moist environment. A continually moist environment can be assured by immersing the cover slip during the mechanical etching of the channels.

In the preferred embodiment, cell plating to the extracellular matrix occurs before the channels are mechanically etched. There is a reason for this order.

If the mechanical etching is done first, and the plating is done second, some cells that settle within the plating area will attach to the mechanically etched channels where the extracellular material has been removed. The cells within the channel areas, lacking the extracellular matrix, will become detached and float in the liquid. At least some of these cells floating within the liquid will eventually land on surfaces of the substrate that have the extracellular matrix. After such landing, they will attach to the regular growth surface and become normal migratory cells, indistinguishable from the cell group under observation. This will introduce new cells into the controlled growth areas which will degrade the controlled observation process of cell proliferation.

By plating the cells on the extracellular matrix, and then removing the plated cells with the extracellular matrix within the channel areas, the phenomena of detached cells floating in the liquid is minimized.

A specialized apparatus is disclosed for mechanically etching regularly spaced intersecting channels onto the extracellular matrix on the substrate. Specifically, an open chamber is defined on the cover slip overlying the extracellular matrix. This open chamber has a fluid tight boundary about the periphery of the chamber to maintain liquid media within the chamber. An etching tool has an etching end with regularly spaced flat mechanical etching teeth separated by regularly spaced intervals for etching the extracellular matrix. The chamber is supplied with a rectilinear opening having boundaries for guiding the etching end of the etching apparatus in movement across the substrate. The etching apparatus has a width to fit snugly within the dimension of the rectilinear opening.

In use, the chamber is placed over the extracellular matrix on the substrate and filled with cell culture media. At least one etching tool with its regularly spaced flat mechanical etching teeth is fitted to the rectilinear opening and extends through the liquid to the substrate. The etching tool is guided by the rectilinear opening and mechanically etches the extracellular matrix while undergoing guided etching excursion across the rectilinear opening. By first having a mechanical etching tool undergo guided etching excursion parallel to first opposite sides of the rectilinear opening and then having a mechanical etching tool undergo excursion parallel to second opposite sides of the rectilinear opening, a regular matrix of channels is defined upon the extracellular matrix. This leaves a pattern of uniformly sized and aligned rectilinear islands upon the extracellular matrix for the isolation of migratory cell growth.

In the normal case, the rectilinear opening is square and a single mechanical etching tool is utilized. It will be understood that two etching tools having varying widths and teeth of varying dimension and spacing can be used to generate rectangular growth areas of varied dimensions.

DESCRIPTION OF THE PREFERRED EMBODIMENTS

Figure 1:
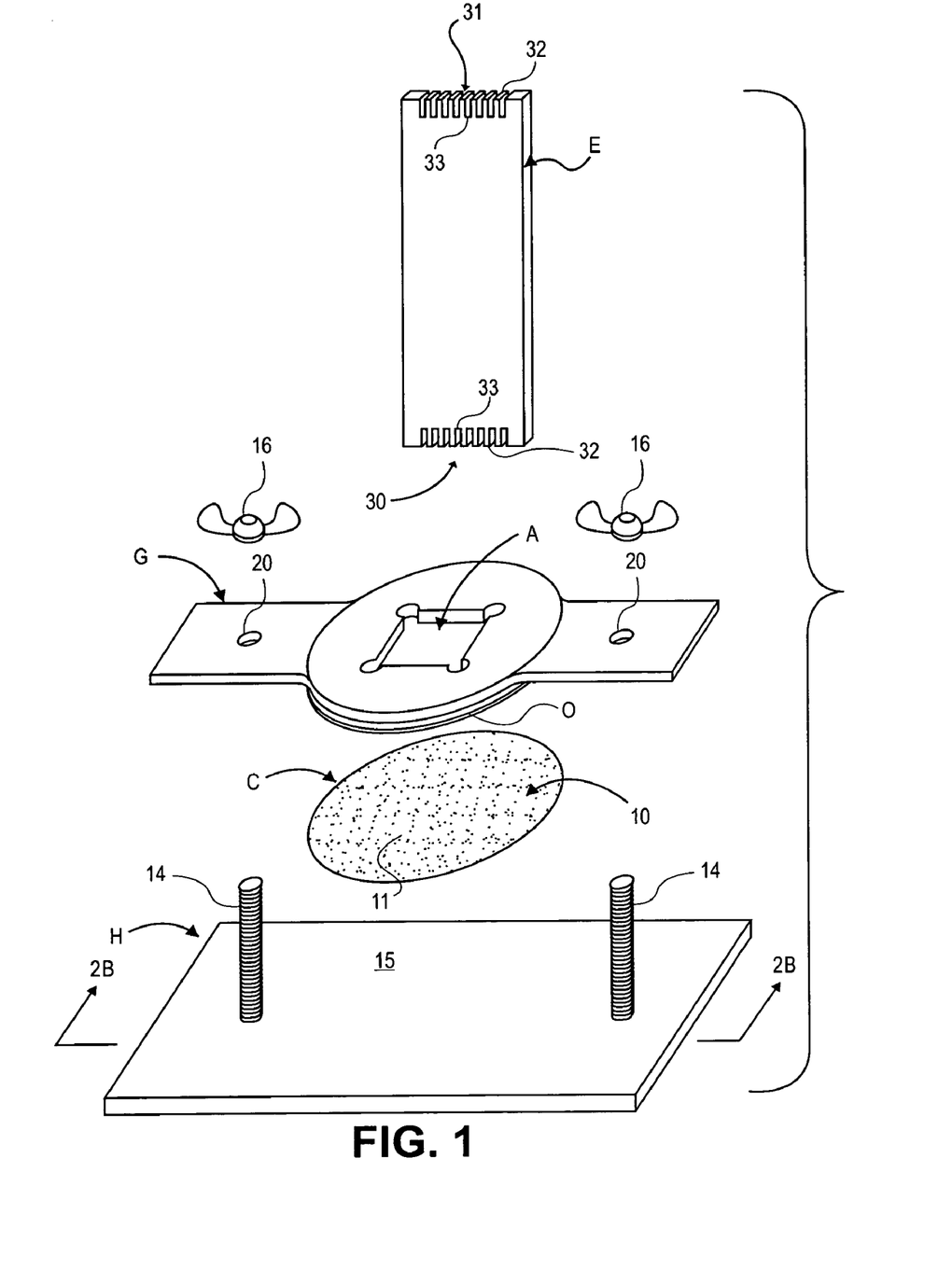
FIG. 1 is an exploded view of a holding plate, a cover slip coated with an extracellular matrix placed upon the holding plate, an O-ring, and overlying cell grid making guide and, an etching tool aligned for etching excursion to configure a first set of channels within the extracellular matrix.

Referring to the exploded view of FIG. 1, holding plate H is shown with cover slip C overlying the holding plate. Typically, cover slip C has an upwardly exposed surface 10 onto which extracellular matrix 11 is adhered and layered. Typically, this extracellular matrix 11 includes two layers including poly-L-ornithine which binds to the upper surface of glass cover slip C and a covering layer of fibronectin which provides the surface for attachment of the cells.

The extracellular matrix 11 is a growth surface. In order to effectively capture cells and thereafter permit the optimum propagation of the captured cells, this surface should preferably remain moist at all times. Because of this requirement, it will be seen that the chamber for etching the desired isolated islands is designed to have the O-ring boundary maintaining the surface of cover slip C in a fluid environment. Immediately overlying cover slip C, circular O-ring O provides a reservoir barrier immediately underlying grid making guide G.

Grid making guide G fastens at apertures 20 to screws 14 protruding upwardly of holding plate H. Grid making guide G includes central bulbous portion having rectilinear aperture A, here shown as a square, configured centrally of the guide. As will hereinafter become apparent, cover slip C is placed on the holding plate H with O-ring O overlying upwardly exposed surface 10 and extracellular matrix 11. Typically, holding plate H, cover slip C, 0-ring O, and grid making guide G are all held together by wing nuts 16 on screws 14 to provide a gentle but firm compression on cover slip C toward holding plate H.

Etching tool E includes first etching end 30 and second etching end 31. Each of these etching ends includes seven regularly thick etching tines 32 spaced by regular intervals 33. Further, etching tool E has an overall width which matches the overall width of square aperture A within grid making guide G. It will be seen that the tines 32 and intervals 33 vary at each end of etching tool E.

In operation, cover slip C is covered with the extracellular matrix and thereafter plated over the surface of the extracellular matrix with the cells to be analyzed during proliferation. Once this is done, holding plate H, cover slip C, O-ring O, and grid making guide G are all assembled, and a liquid is poured into the chamber defined between cover slip C and grid making guide G by O-ring O. Thereafter, mechanical etching occurs utilizing an end 30, 31 of etching tool B. This etching occurs by aligning etching tool E parallel to one of the sides of aperture A and moving the tool normal to its parallel alignment. This movement places a group of channels L (see FIG. 5) across the surface of cover slip C. Thereafter, by rotating etching tool E 90°, and repeating the movement of the tool normal to its parallel alignment, a second set of intersecting channels L is placed across cover slip C. Since these intersecting channels L will be at 90° with respect to the earlier etched channels L, the remaining extracellular matrix will form isolated islands I or I1 (See FIGS. 5 and 6 at respective islands I and I1). It has been found that these isolated islands I and I1 permit isolated populations of migratory cells to propagate without substantial migration either from without the boundaries of the islands or from within the boundaries of the islands to positions exterior of the islands.

Figure 2A:
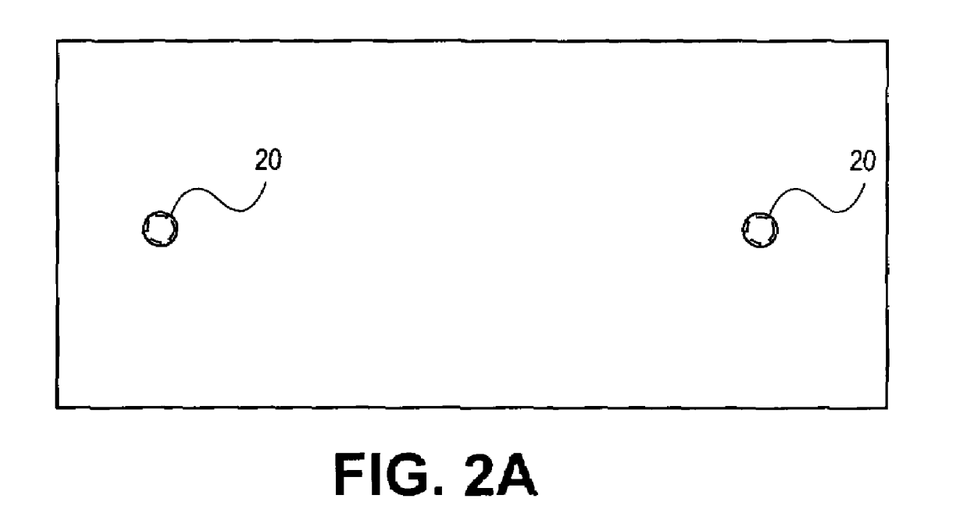
FIGS. 2A and 2B are plan and elevation views of the holding plate, respectively.
Figure 2B:
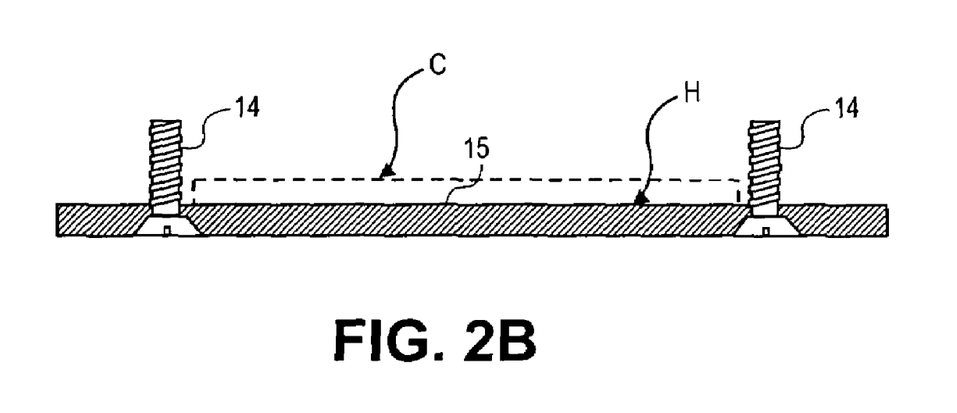

Referring to FIGS. 2A and 2B, holding plate H includes flat plate 15 having respective upstanding bolts 14 mounted thereto. This plate allows a cover slip C to fit conveniently between upstanding bolts 14.

Figure 3A:
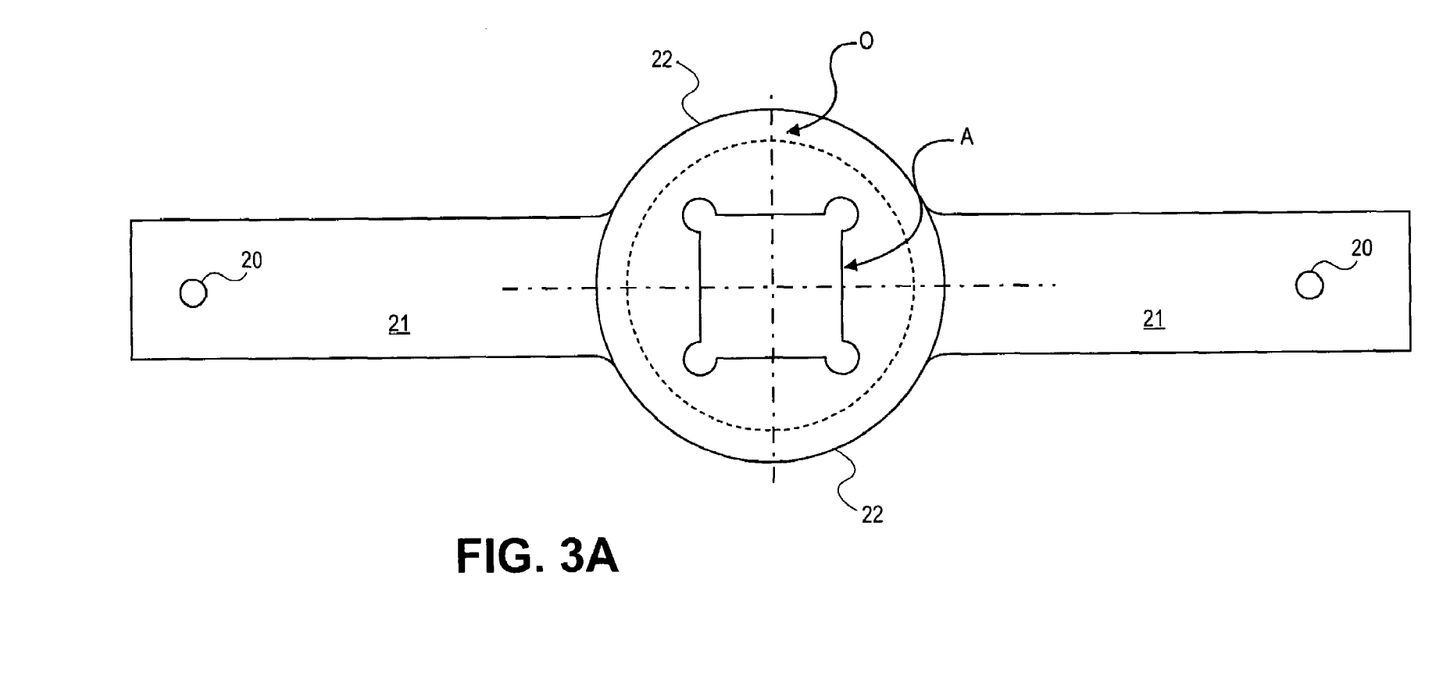
FIGS. 3A and 3B are plan views of cell grid making guides.

Referring to FIG. 3A, a first cell grid making guide G is illustrated. Grid making guide G includes central bulbous portion 22 spanned on either side by wings 21. Apertures 20 accommodating upstanding bolts 14 are configured in the ends of the respective wings 21. O-ring O is shown in broken lines with respect to bulbous portion 22 of cell grid making guide G.

Figure 3B:
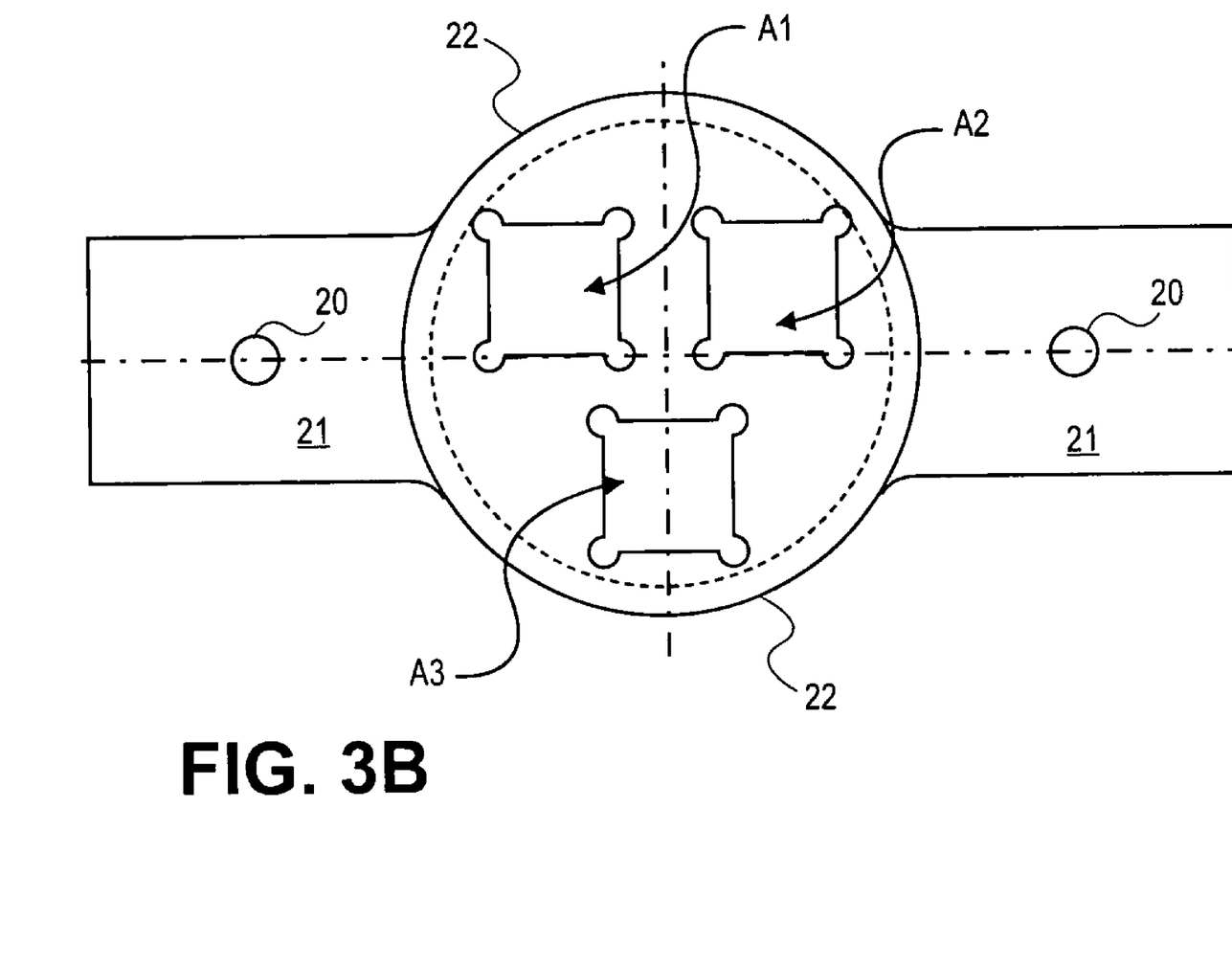

Referring to FIG. 3B, a second cell grid making guide G' is illustrated. In this embodiment central bulbous portion 22 includes three apertures A1, A2, and A3.

Figure 4:
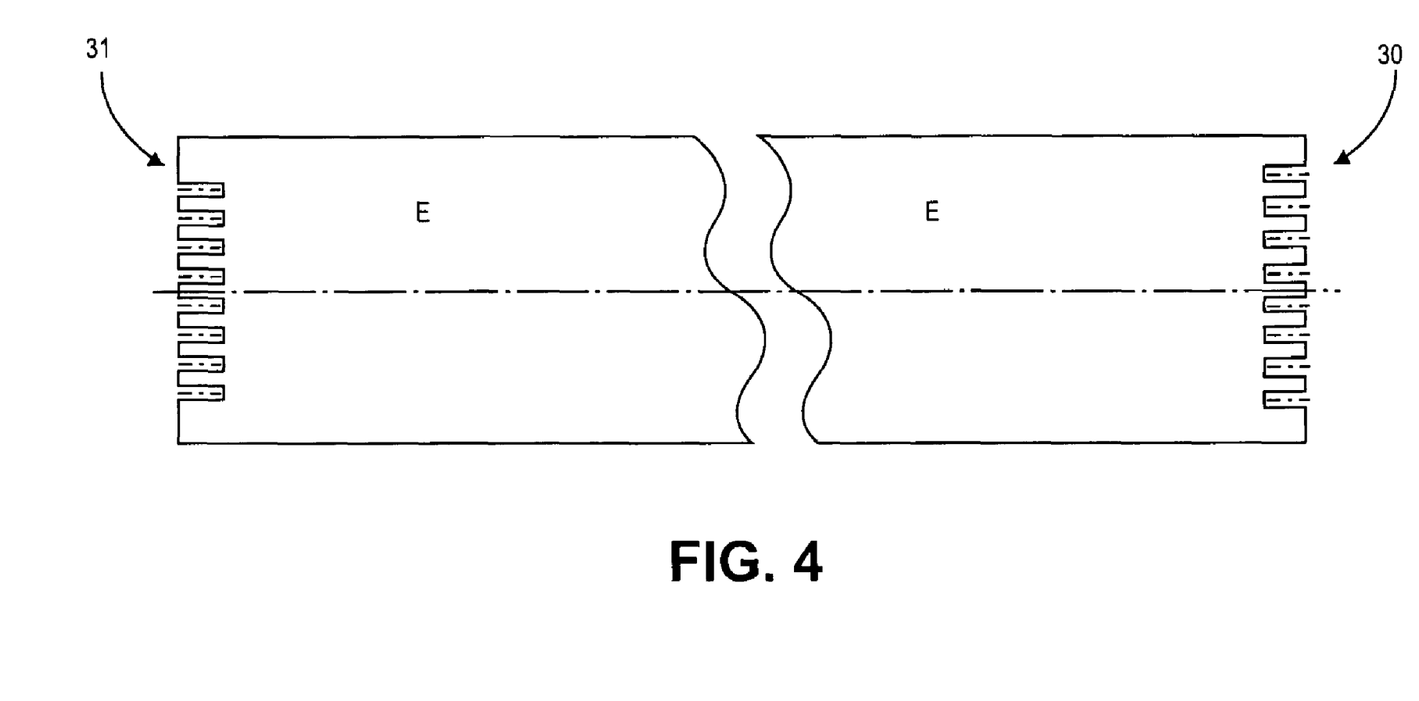
FIG. 4 is a side elevation of an etching tool for excursion within the cell grid making guide of FIG. 3, the tool having etching members at both ends.

Referring to FIG. 4, etching tool E is illustrated. Etching tool E includes two different etching ends 30,31. Observing end 30, it can be seen that etching tines 32 across end 30 are all the same dimension. Further, each etching tine 32 is separated from its adjacent etching tines by regular intervals 33. Comparing end 31 with end 30, it will be seen that the dimensions of the tines 32 and their interval of separation 33 are varied. Dimensions are important. By way of example, the respective tines on end 30 are 0.042 in. center to center spacing with slots 0.022 in there between. Similarly, end 31 includes center to center spacing of the tines at 0.038 in. with slots of 0.018 in. there between. The etching tool E is approximately 10 mm wide by 100 millimeters long and made of 1/16 in stainless steel.

Figure 5:
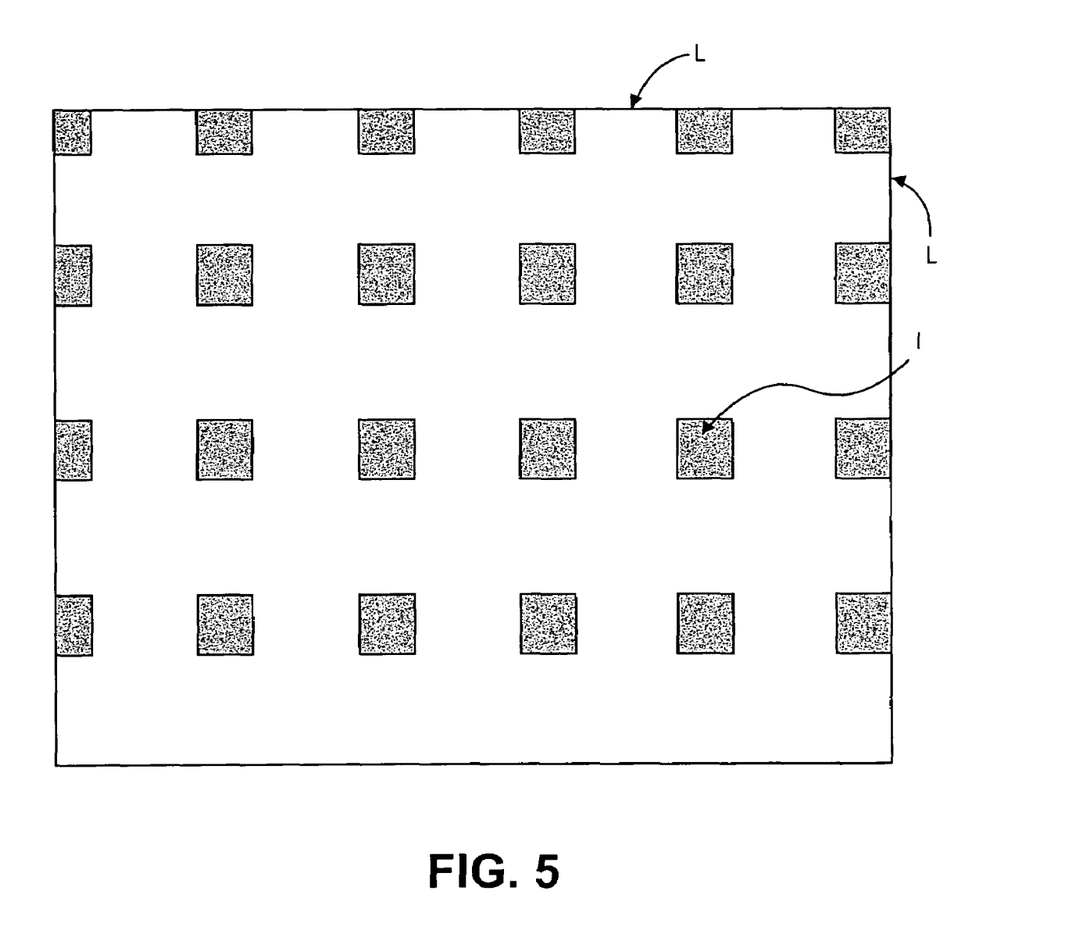
FIG. 5 is a plan view of multiple restricted-growth areas generated as a grid on an observation cover slip.
Figure 6:
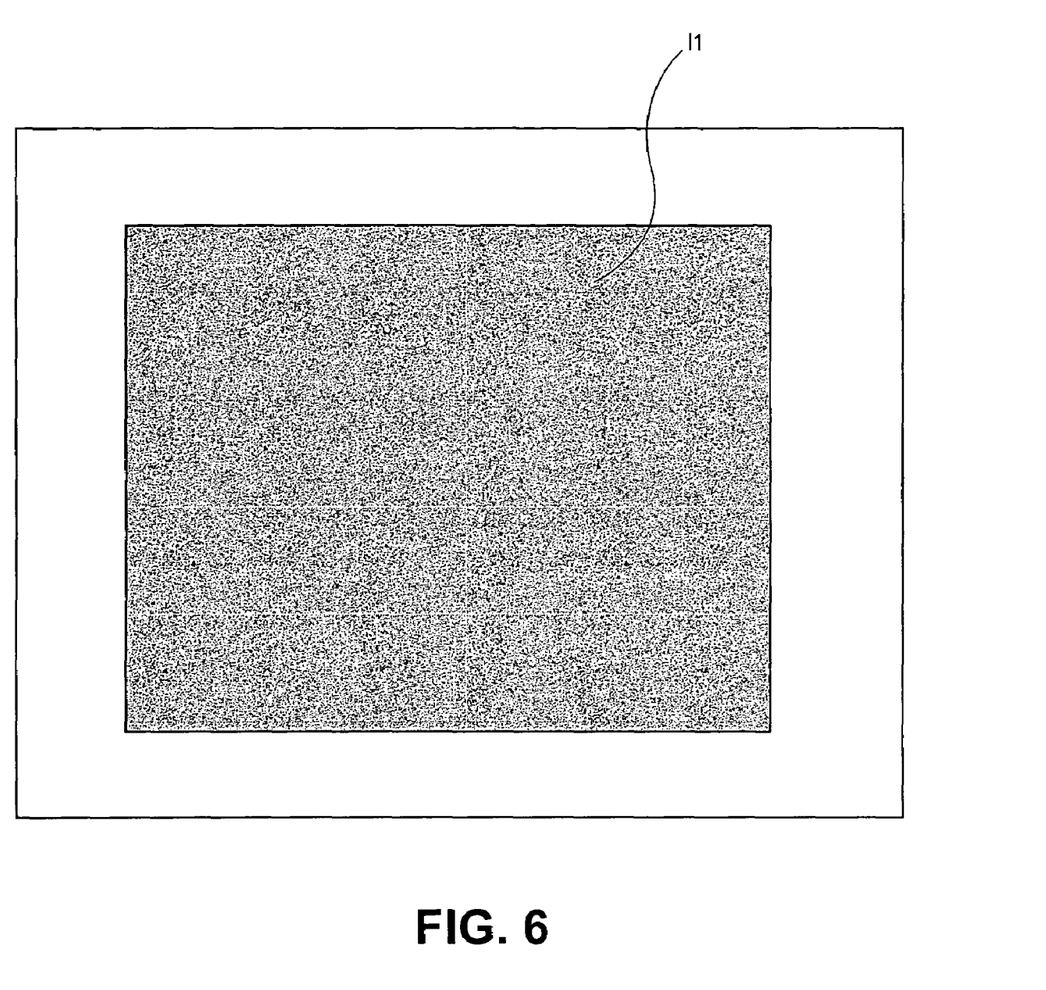
FIG. 6 is a plan view of a single rectilinear growth area configured by utilizing a first end of the etching tool shown in FIG. 4 for a vertical channels and a second end of the etching tool shown in FIG. 4 for horizontal channels.

Referring to FIG. 5, the end result of the etching process can be seen. Specifically, isolated islands I of the extracellular matrix are illustrated. Referring to FIG. 6, a rectilinear island I1 is illustrated. Rectilinear islands can be formed by using one end 30 of etching tool E for etching in one direction, and the other end 31 of the etching tool E for etching in the other direction at 90° to the first direction.

Figure 7A:
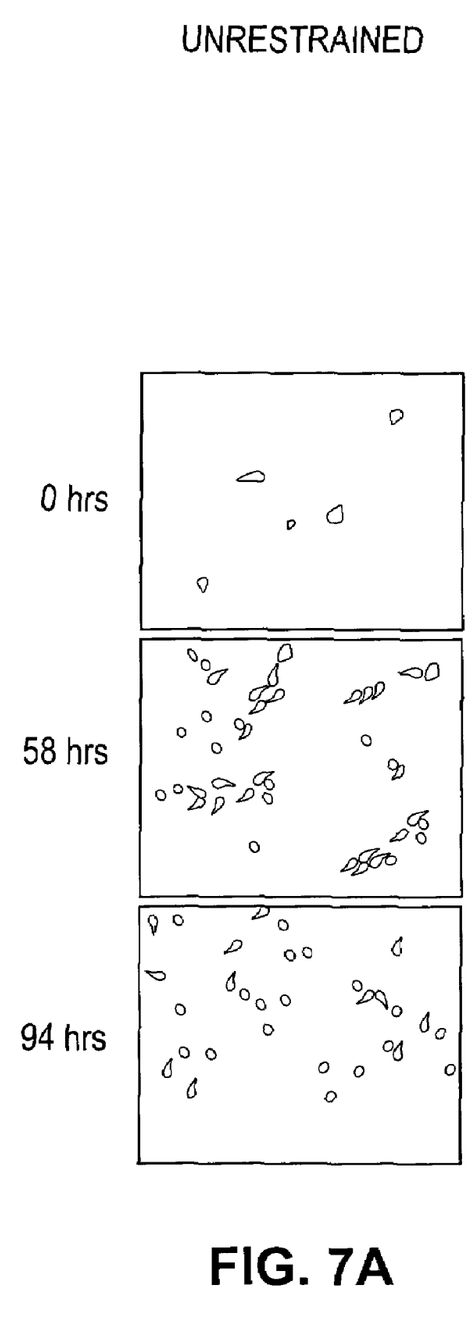
FIGS. 7A and 7B are a matrix of unrestrained and restrained growth islands and timed intervals illustrating the cell monitoring permitted by this invention; and, FIGS. 8A and 8B are a lineage analysis for cells of the unrestrained and restrained growth islands illustrating the superior monitoring of this invention.
Figure 7B:
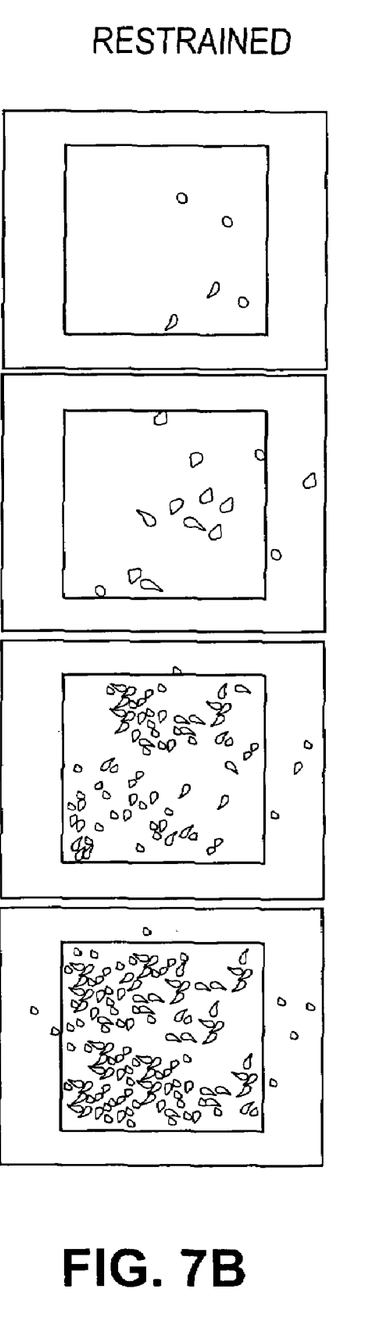

Referring to FIGS. 7A and 7B, the remarkably different population result from the growing of migratory cells is illustrated. Specifically, and observing FIG. 7A, where the surface of the extracellular matrix is without islands I, cell distribution is sparse. Conversely, and observing FIG. 7B, where the surface of the extracellular matrix is with islands I, cell distribution is dense.

During proliferation, the areas in which the cells grow are monitored continuously. Where cells leave the monitored areas, there is no way of identifying what happens to the cells. Where the cells arrive into the monitored areas, there is no way of identifying what is the prior history of the cells and where they have come from.

Where the islands I set forth in this disclosure are utilized, cells are for the most part confined to the boundaries of the islands. Presuming that the entirety of the islands are continuously monitored, departing and arriving cells are essentially eliminated enabling a much more comprehensive record of proliferation to be maintained.

Figure 8A:
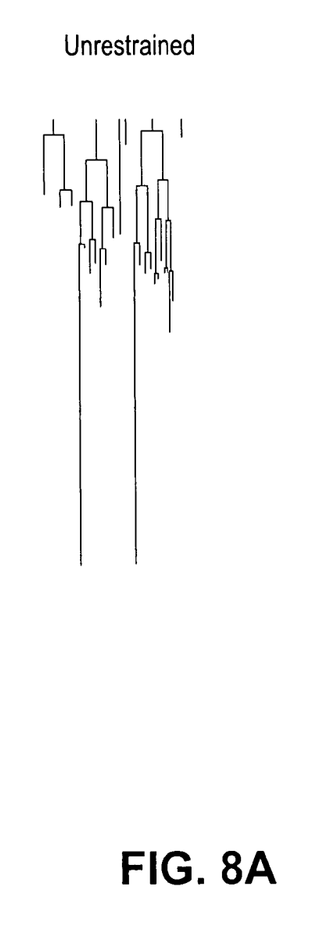
Figure 8B:
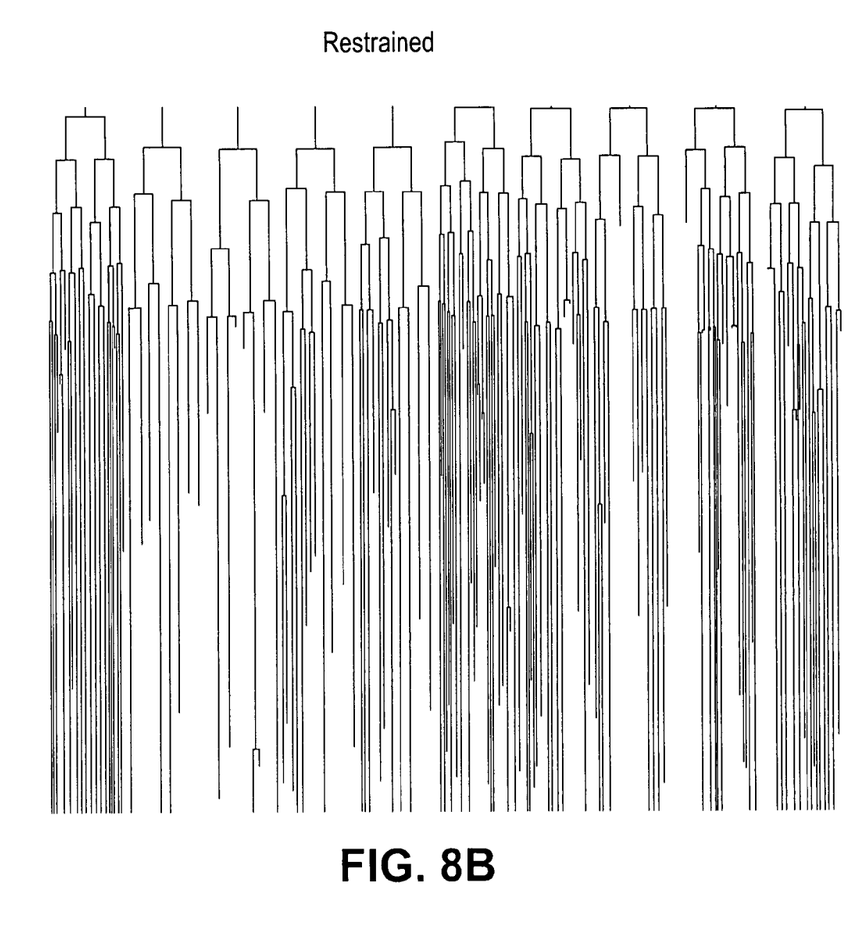

The results of this latter assurance can be seen in the graphical representation of FIGS. 8A and 8B. Observing FIG. 8A, it will be seen that in a lineage diagram, or family tree, of the original cells (approximately six) shown, only two derivatives remaining in the final frame of the recording. All other cells leave the visual field or die.

Observing FIG. 8B, it will be seen that the restrained population differs radically. The observed population is much more numerous. Furthermore, cells are illustrated can be tracked to the seventh generation, as distinguished from a mere three generations.

What is claimed is:

1. A process for restricting migration of migratory cells on a substrate comprising the steps of:
   providing a flat substrate;
   coating the substrate with extracellular matrix;
   plating migratory cells onto the extracellular matrix to create a matrix with cells;
   allowing the cells to adhere to the extracellular matrix; and,
   thereafter placing intersecting channels across the matrix with cells by etching in an intersecting channel pattern to isolate islands containing matrix with cells on the substrate.

2. The process for restricting migration of migratory cells on a substrate according to claim 1 and wherein said intersecting channels are mechanically etched with an etching tool within said matrix with cells.

3. The process for restricting migration of migratory cells on a substrate according to claim 2 and wherein said etching tool has a plurality of etching tines to mechanically etch said matrix with cells.

4. The process for restricting migration of migratory cells on a substrate according to claim 1 and wherein said matrix with cells is submerged in liquid during the placement of intersecting channels within said matrix with cells.

5. The process for restricting migration of migratory cells on a substrate according to claim 4 wherein said liquid is cell culture media.

* * * * *